United States Patent
Rock (10) Patent No.: US 10,296,722 B2
(45) Date of Patent: *May 21, 2019

(54) VIRTUAL REHABILITATION SYSTEM AND METHOD

(71) Applicant: Eric Rock, Plano, TX (US)

(72) Inventor: Eric Rock, Plano, TX (US)

(73) Assignee: VIVIFY HEALTH, INC., Plano, TX (US)

( * ) Notice: Subject to any disclaimer, the term of this patent is extended or adjusted under 35 U.S.C. 154(b) by 686 days.

This patent is subject to a terminal disclaimer.

(21) Appl. No.: 14/224,666

(22) Filed: Mar. 25, 2014

(65) Prior Publication Data

US 2014/0295392 A1   Oct. 2, 2014

Related U.S. Application Data

(63) Continuation-in-part of application No. 14/223,815, filed on Mar. 24, 2014, and a continuation-in-part of (Continued)

(51) Int. Cl.
*G06F 19/00* (2018.01)

(52) U.S. Cl.
CPC ...... *G06F 19/3481* (2013.01); *G06F 19/3418* (2013.01)

(58) Field of Classification Search
CPC ............ G06F 19/3487; G06F 19/3481; G06F 19/322; G06F 17/30793; A61B 8/06
(Continued)

(56) References Cited

U.S. PATENT DOCUMENTS 5,940,801 A   8/1999   Brown
7,593,952 B2  9/2009   Soll et al.
(Continued)

FOREIGN PATENT DOCUMENTS

WO   WO 2013033655 A1   3/2013

OTHER PUBLICATIONS

Doukas, et. al., "Mobile Healthcare Information management Utilizing Cloud Computing and Android OS"; 32nd Annual International Conference of the IEEE EMBS Buenos Aires, Argentina, Aug. 31-Sep. 4, 2010.

*Primary Examiner* — Hiep V Nguyen
(74) *Attorney, Agent, or Firm* — David W. Carstens; James D. Tuck; Carstens & Cahoon, LP (57) ABSTRACT

A system and method providing virtual physical rehabilitation services to a patient in the context of automated patient healthcare delivery is disclosed. The system/method are controlled by a patient healthcare plan (PHP) deployed from a host computer system (HCS) that triggers execution of a video script dataset (VSD) to coordinate presentation to a patient of rehabilitation audio/video information (AVI) derived from a video database (VDB). A mobile user device (MUD) executes the PHP autonomously to coordinate AVI display on a video display unit (VDU) for patient presentation. Patient reactions to the AVI are observed by a video imaging unit (VIU). An operator interface computer (OIC) communicates with the HCS and MUD permitting visualization of the VIU and AVI information by a healthcare provider and allowing observed patient behavior to be synchronously scored/logged/stored in a patient history database (PHD) by the HCS.

24 Claims, 8 Drawing Sheets

Related U.S. Application Data application No. 14/223,537, filed on Mar. 24, 2014, and a continuation-in-part of application No. 14/223,652, filed on Mar. 24, 2014, now Pat. No. 9,357,238, and a continuation-in-part of application No. 14/223,747, filed on Mar. 24, 2014.

(60) Provisional application No. 61/805,355, filed on Mar. 26, 2013.

(58) Field of Classification Search
USPC .......................................................... 705/2
See application file for complete search history.

(56) References Cited

U.S. PATENT DOCUMENTS

| | | | |
|---|---|---|---|
| 7,739,126 B1 | 6/2010 | Cave et al. | |
| 8,183,998 B2 | 5/2012 | Rao et al. | |
| 8,239,903 B1 | 8/2012 | Campagna et al. | |
| 8,301,233 B2 | 10/2012 | Zhang et al. | |
| 8,321,808 B2 | 11/2012 | Goetz et al. | |
| 8,326,651 B2 | 12/2012 | McLaren et al. | |
| 8,396,804 B1 | 3/2013 | Dala et al. | |
| 2002/0184055 A1 | 12/2002 | Naghavi et al. | |
| 2003/0022141 A1 | 1/2003 | Packard | |
| 2003/0176790 A1* | 9/2003 | Slayton | A61B 8/00 600/439 |
| 2004/0039254 A1 | 2/2004 | Stivoric et al. | |
| 2004/0102931 A1 | 5/2004 | Ellis et al. | |
| 2005/0102160 A1 | 5/2005 | Brown | |
| 2005/0283385 A1 | 12/2005 | Hunkeler et al. | |
| 2006/0030890 A1 | 2/2006 | Cosentino et al. | |
| 2006/0234202 A1 | 10/2006 | Brown | |
| 2007/0006322 A1 | 1/2007 | Karimzadeh et al. | |
| 2007/0015974 A1 | 1/2007 | Higgins et al. | |
| 2007/0191070 A1 | 8/2007 | Rao | |
| 2007/0255345 A1 | 11/2007 | Krause | |
| 2008/0077436 A1 | 3/2008 | Muradia | |
| 2008/0242947 A1 | 10/2008 | Jung et al. | |
| 2008/0275317 A1 | 11/2008 | Cho et al. | |
| 2008/0281633 A1* | 11/2008 | Burdea | A61B 5/0002 705/2 |
| 2009/0150416 A1 | 6/2009 | Baker et al. | |
| 2011/0029327 A1 | 2/2011 | Dunlop | |
| 2011/0166884 A1 | 7/2011 | Lesselroth et al. | |
| 2011/0234409 A1 | 9/2011 | Soliman | |
| 2011/0238435 A1 | 9/2011 | Rapaport et al. | |
| 2011/0295621 A1 | 12/2011 | Farooq et al. | |
| 2012/0041771 A1 | 2/2012 | Cosentino et al. | |
| 2012/0183941 A1 | 7/2012 | Steinmetz | |
| 2012/0203573 A1 | 8/2012 | Mayer et al. | |
| 2013/0035955 A1 | 2/2013 | Torres | |
| 2013/0138450 A1* | 5/2013 | Vigneux | G06Q 10/00 705/2 |
| 2013/0262155 A1 | 10/2013 | Hinkamp | |
| 2013/0329058 A1 | 12/2013 | Brossette et al. | |
| 2013/0339060 A1 | 12/2013 | Delaney et al. | |
| 2016/0006946 A1* | 1/2016 | Cohen | G06F 19/326 348/660 |

* cited by examiner

VIRTUAL REHABILITATION SYSTEM AND METHOD

CROSS REFERENCE TO RELATED APPLICATIONS

U.S. Provisional Patent Applications

This application claims benefit under 35 U.S.C. § 119 and incorporates by reference U.S. Provisional Patent Application for HEALTHCARE MANAGEMENT SYSTEM AND METHOD by inventor Eric Rock, filed electronically with the USPTO on Mar. 26, 2013, with Ser. No. 61/805,355, EFS ID 15358332, confirmation number 6386.

U.S. Utility Patent Applications

This application claims benefit under 35 U.S.C. § 120 and incorporates by reference U.S. Utility patent application for HEALTHCARE DELIVERY SYSTEM AND METHOD by inventor Eric Rock, filed electronically with the USPTO on Mar. 24, 2014, with Ser. No. 14/223,537, EFS ID 18566754, confirmation number 2107. This patent application will be referred to herein as the HEALTHCARE DELIVERY SYSTEM AND METHOD patent application.

This application claims benefit under 35 U.S.C. § 120 and incorporates by reference U.S. Utility patent application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

This application claims benefit under 35 U.S.C. § 120 and incorporates by reference U.S. Utility patent application for DYNAMIC VIDEO SCRIPTING SYSTEM AND METHOD by inventor Eric Rock, filed electronically with the USPTO on Mar. 24, 2014, with Ser. No. 14/223,815, EFS ID 18568932, confirmation number 2060. This patent application will be referred to herein as the DYNAMIC VIDEO SCRIPTING SYSTEM AND METHOD patent application.

This application claims benefit under 35 U.S.C. § 120 and incorporates by reference U.S. Utility patent application for MEDICATION RECONCILIATION SYSTEM AND METHOD by inventor Eric Rock, filed electronically with the USPTO on Mar. 24, 2014, with Ser. No. 14/223,747, EFS ID 18568406, confirmation number 1061. This patent application will be referred to herein as the MEDICATION RECONCILIATION SYSTEM AND METHOD patent application.

U.S. Continuation-in-Part (CIP) Patent Application

This application is a continuation-in-part (CIP) patent application of and incorporates by reference U.S. Utility patent application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

This application is a continuation-in-part (CIP) patent application of and incorporates by reference U.S. Utility patent application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

This application is a continuation-in-part (CIP) patent application of and incorporates by reference U.S. Utility patent application for DYNAMIC VIDEO SCRIPTING SYSTEM AND METHOD by inventor Eric Rock, filed electronically with the USPTO on Mar. 24, 2014, with Ser. No. 14/223,815, EFS ID 18568932, confirmation number 2060. This patent application will be referred to herein as the DYNAMIC VIDEO SCRIPTING SYSTEM AND METHOD patent application.

This application is a continuation-in-part (CIP) patent application of and incorporates by reference U.S. Utility patent application for MEDICATION RECONCILIATION SYSTEM AND METHOD by inventor Eric Rock, filed electronically with the USPTO on Mar. 24, 2014, with Ser. No. 14/223,747, EFS ID 18568406, confirmation number 1061. This patent application will be referred to herein as the DYNAMIC VIDEO SCRIPTING SYSTEM AND METHOD patent application.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for implementing patient rehabilitation services, and specifically to provide such services in the context of remotely monitored patient healthcare delivery. Without limiting the scope of the present invention, the present invention may be advantageously applied to the following U.S. Patent Classifications: 340/573.1; 340/407.1; 434/114; 345/473; 482/1; and 601/1.

PRIOR ART AND BACKGROUND OF THE INVENTION

Prior Art System Context

Within the context of healthcare delivery systems there is often a need for healthcare professionals to gauge the degree of rehabilitation that a patient has undergone as a follow-up to surgery or some other medical procedure. This patient evaluation may involve determining baseline range-of-motion measurements as well as various programs of physical therapy in which the patient performs repetitive motions under the direction of a physical therapist. This rehabilitation context often occurs outside the context of a normal healthcare delivery by a primary physician or other healthcare provider team and is performed by a physical therapist.

Often the physician in charge of patient care has limited contact with the physical therapist and this limited communication may result in inadequate responses to declines in patient condition or failure to address serious issues regarding the overall rehabilitation of the patient. Additionally, in many circumstances transportation of the patient to the physical therapist is problematic in that the patient lacks transportation or has mobility limitations. This often prevents the patient from receiving adequate rehabilitation that meets their individual needs.

Deficiencies in the Prior Art

The prior art as detailed above suffers from the following deficiencies:
- Prior art virtual rehabilitation systems and methods do not permit remote rehabilitation for patients unable to meet with a physical therapist.
- Prior art virtual rehabilitation systems and methods cannot operate autonomously in conjunction with an overall patient healthcare plan (PHP).
- Prior art virtual rehabilitation systems and methods do not provide a standardized metric for patient progress.
- Prior art virtual rehabilitation systems and methods do not allow the physician in charge to directly monitor patient rehabilitation progress.
- Prior art virtual rehabilitation systems and methods do not permit the physician in charge to define the aggressiveness of patient rehabilitation.
- Prior art virtual rehabilitation systems and methods do not integrate virtual rehabilitation into an overall automated patient healthcare plan (PHP).

While some of the prior art may teach some solutions to several of these problems, the core issue of virtualizing patient rehabilitation in the context of an overall unified patient healthcare plan (PHP) has not been solved by the prior art.

Objectives of the Invention

Accordingly, the objectives of the present invention are (among others) to circumvent the deficiencies in the prior art and affect the following objectives in the context of a virtual rehabilitation system and method:
(1) Provide for a virtual rehabilitation system and method that permits remote rehabilitation for patients unable to meet with a physical therapist.
(2) Provide for a virtual rehabilitation system and method that operates autonomously in conjunction with an overall patient healthcare plan (PHP).
(3) Provide for a virtual rehabilitation system and method that permits a standardized metric for patient progress.
(4) Provide for a virtual rehabilitation system and method that permits the physician in charge to directly monitor patient rehabilitation progress.
(5) Provide for a virtual rehabilitation system and method that permits the physician in charge to define the aggressiveness of patient rehabilitation.
(6) Provide for a virtual rehabilitation system and method that integrates virtual rehabilitation into an overall automated patient healthcare plan (PHP).

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention addresses patient rehabilitation by virtualizing the patient-therapist interaction and standardizing both the rehabilitation directives provided to the patient and the scoring of patient progress that is typically measured by the therapist/healthcare provider. The present invention as embodied in a system provides for a healthcare computer system (HCS) that disseminates a patient healthcare plan (PHP) to a mobile user device (MUD) for operation in an autonomous fashion with respect to the delivery of patient healthcare. The PHP as part of its autonomous operation on the MUD executes a video script dataset (VSD) that incorporates structured audio/video information (AVI) presented to the patient. The VSD is formed on the HCS under control of healthcare providers and is generated via a GUI editor as described in the DYNAMIC VIDEO SCRIPTING SYSTEM AND METHOD patent application incorporated herein.

The AVI content is displayed to the patient using a user interaction context (UIC) as described in the VIDEO DATA EXTENSION SYSTEM AND METHOD patent application incorporated herein. This UIC may incorporate displays on the MUD and/or a video display unit (VDU) to present the AVI to the patient. The patient then responds to the AVI content that typically incorporates directives for patient rehabilitation motion, exercises, etc. These patient responses are captured with a video input unit (VIU) to generate a patient imaging input (PII) that is relayed to an operator interface computer (OIC) for display to a healthcare provider.

The healthcare provider is presented with synchronized visual displays representing the AVI, the PII, and a results scoring display that allows the healthcare provider to score the patient responses and provide additional comments on the patient rehabilitation progress. The results scoring input from the healthcare provider may be scripted by the PHP and/or the VSD to provide set milestone guideposts for the measurement of patient rehabilitation. The results of this patient scoring by the healthcare provider is then sent to the HCS for storage in the patient history database (PHD) that may then be viewed by healthcare providers, physicians, and other individuals responsible for healthcare delivery to the patient.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a VIRTUAL REHABILITATION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

System Overview (0100)

Figure 1:
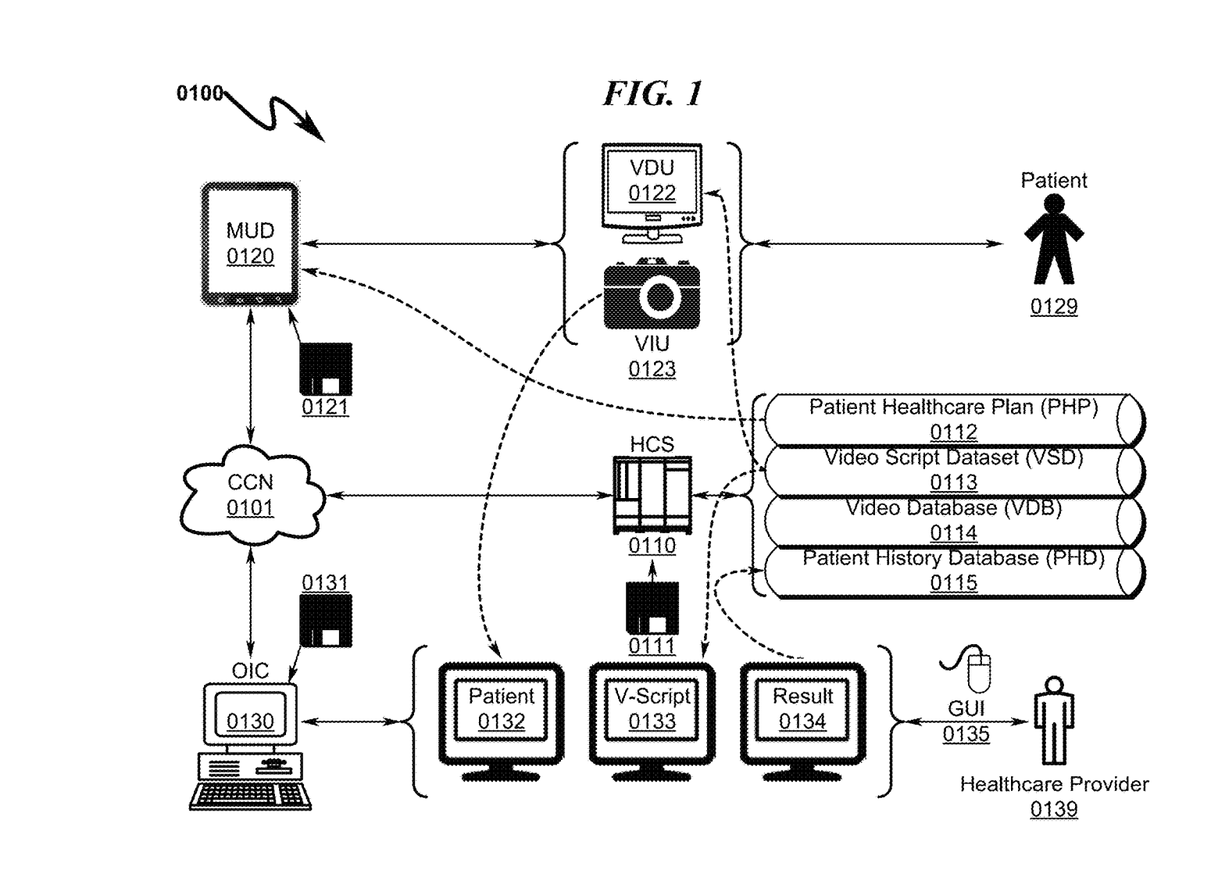
FIG. 1 illustrates an overview block diagram depicting an exemplary virtual rehabilitation system.

The present invention may be summarized as depicted in the system block diagram of FIG. 1 (0100), and is comprised of three cooperating computer systems as depicted by the host computer system (HCS) (0110), mobile user device (MUD) (0120), and operator interface computer (OIC) (0130). Each of these computer systems (0110, 0120, 0130) operates under control of machine instructions read from computer readable medium (0111, 0121, 0131). Within this context the host computer system (HCS) (0110) works in conjunction with the MUD (0120) to deploy a patient healthcare plan (PHP) (0112) for execution on the MUD (0120). The PHP (0112) may comprise one or more video script datasets (VSD) (0113) that describe an interaction with a patient (0129) via the controlled display of audio/video information (AVI) extracted from a video database (VDB) (0114). This AVI data is transmitted to a video display unit (VDU) (0122) under control of the MUD (0120) and presented to the patient (0129).

The patient (0129) is observed by a video input unit (VIU) (0123) in response to VSD (0113) information that dictates one or more controlled rehabilitation therapies. The AVI display data and VIU (0123) input is transmitted to the OIC (0130) where it is displayed (0132, 0133) along with the AVI content to a healthcare provider (0139). The healthcare provider (0139) then interacts with a synchronized script to enter scoring information associated with the performance of the patient (0129) in response to the scripted VDU (0122) display. This scoring information is then transmitted to the HSC (0110) for storage in a patient history database (PHD) (0115).

Within this context the rehabilitation process experienced by the patient (0129) may be dictated by VSD (0113) scripts under control of a more global PHP (0112) that is tailored to the patient (0129). Additionally, it should be noted that the displays (0132, 0133) and inputs (0134) present on the OIC (0130) may be delayed in time so that the rehabilitation process presented to the patient (0129) may occur at a prior time as compared to the scoring of the patient performance by the healthcare provider (0139).

Method Overview (0200)

Figure 2:
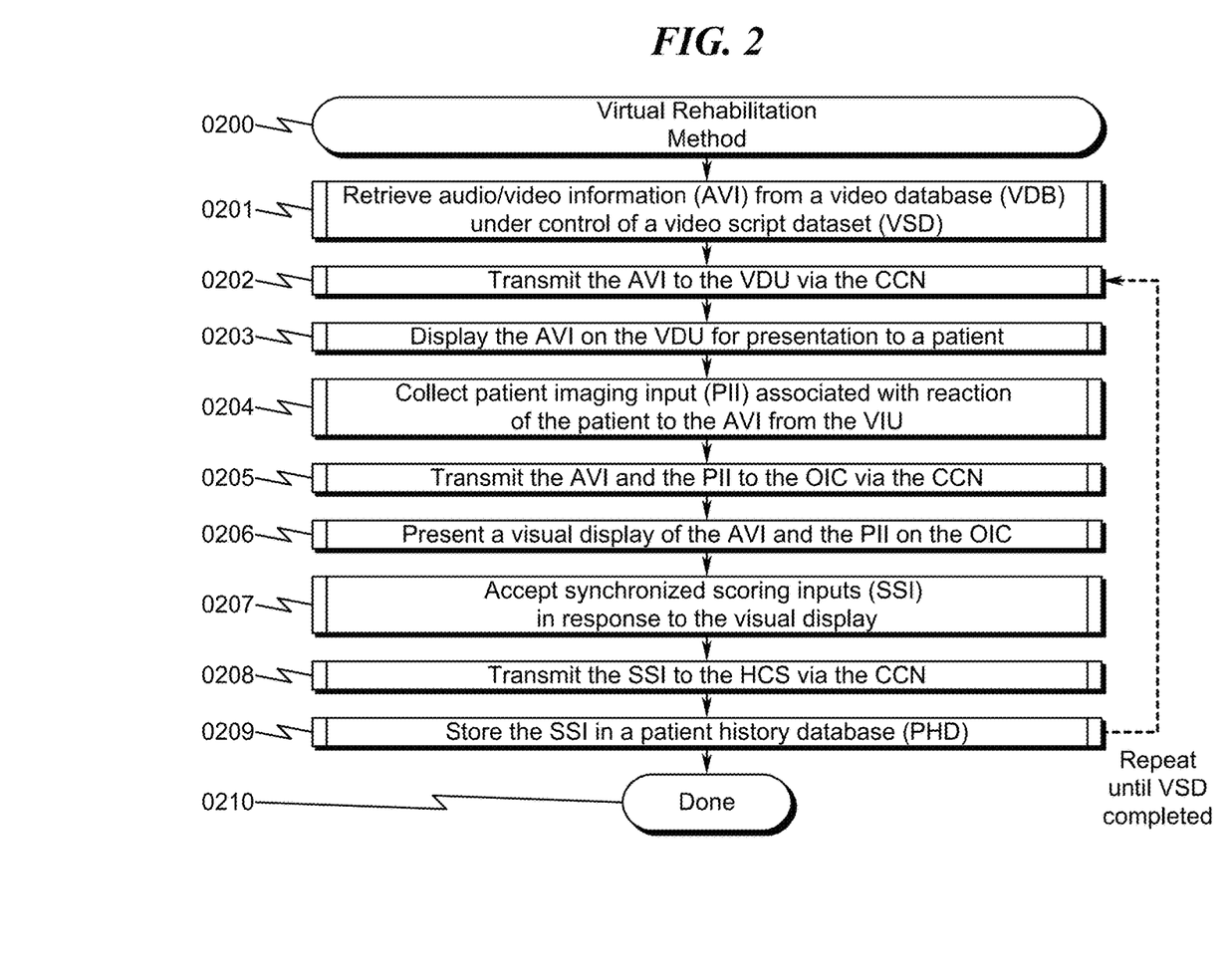
FIG. 2 illustrates a flowchart depicting an exemplary virtual rehabilitation method.

The system context as depicted in FIG. 1 (0100) is typically associated with a methodology as depicted in FIG. 2 (0200) and involves the following steps:
(1) with a host computer system (HCS), retrieving audio/video information (AVI) from a video database (VDB) under control of a video script dataset (VSD) (0201);
(2) with a mobile user device (MUD), coordinating transmission of the AVI to a video display unit (VDU) via a computer communication network (CCN) (0202);
(3) with the MUD, coordinating display of the AVI on the VDU for presentation to a patient (0203);
(4) with the MUD, collecting patient imaging input (PII) associated with reaction of the patient to the AVI from a video imaging unit (VIU) (0204);
(5) with the MUD, coordinating transmission of the AVI and the PII to an operator interface computer (OIC) via the CCN (0205);
(6) with the OIC, presenting a visual display of the AVI and the PII (0206);
(7) with the OIC, accepting synchronized scoring inputs (SSI) responsive to the visual display (0207);
(8) with the OIC, transmitting the SSI to the HCS via the CCN (0208); and
(9) with the HCS, storing the SSI in a patient history database (PHD) (0209).

Note that data contained within the MRD may be collected and updated in real-time from a medical instrumentation device (MID) communicating with the MUD.

System Detail (0300)

Figure 3:
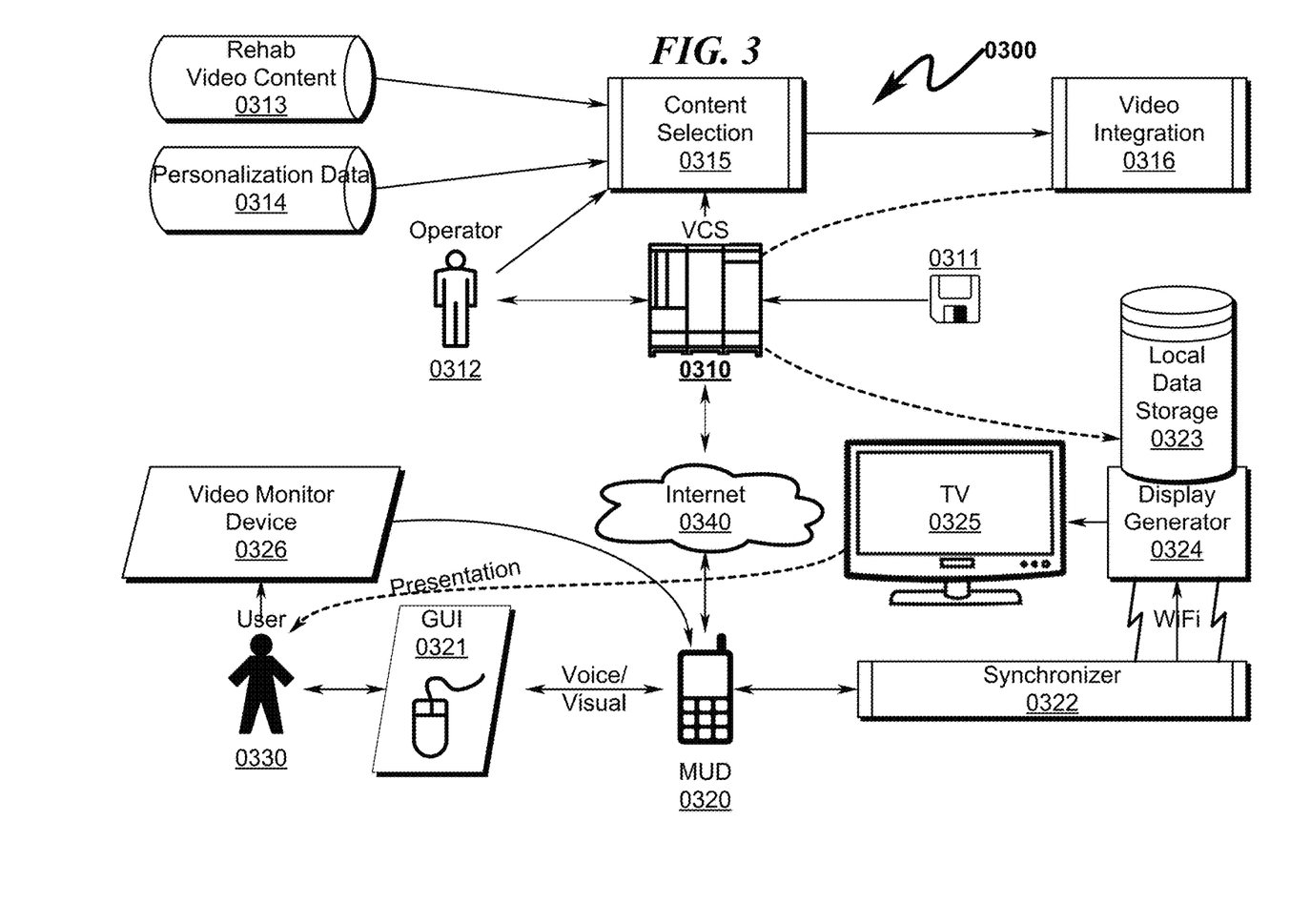
FIG. 3 illustrates a detail block diagram depicting an exemplary virtual rehabilitation system.

As depicted in FIG. 3 (0300) one preferred embodiment of the present invention covers the use of virtual reality and canned video scripts to supervise and monitor the rehabilitation of patients. The use of real-time video feedback between the patient and a healthcare professional is anticipated in this context. This capability may be used in conjunction with the MEDICATION RECONCILIATION SYSTEM AND METHOD patent application to integrate healthcare delivery to the patient in a remote patient healthcare delivery context.

As generally depicted in FIG. 3 (0300), the system may be described as a virtual rehabilitation system comprising:
(a) video content server (VCS) (0310);
(b) mobile user device (MUD) (0330); and
(c) video presentation device (VPD) (0325);
(d) video display generator (VDG) (0324); and
(e) video presentation manager (VPM) (0316);
wherein the VCS is configured to communicate with the MUD through a communication network (0340);

the VCS is configured to select content (0315) from a rehabilitation video content database (0313) and apply personalization data from a personalization database (0314) and distribute the selected content to the VDG (0324) operating under control of a synchronizer process running on the MUD;

the MUD is configured to accept video monitoring input (0326) associated with a user and merge this information with data collected from a graphical user interface (GUI) presented on the MUD to direct the selected content from the VCS over the communication network;

the VCS support an operator (0312) interface to permit direction of the user in response to video input received from the video monitoring input; and the VDG is configured to accept video content from the VCS under control of the VPM and present the video content to a video display.

This system as described may integrate aspects of the VIDEO DATA EXTENSION SYSTEM AND METHOD patent application to provide for a user interaction context (UIC) that spans the MUD and VDU so that certain aspects of the deployed AVI to the patient are spread among these various input/output devices. Furthermore, the use of video scripting as described in the DYNAMIC VIDEO SCRIPTING SYSTEM AND METHOD patent application permits complex scripting of the rehabilitation session with the patient, and may coordinate patient inputs, direct communication with a live physician, or other complex tasks based within a video script that coordinates the patient/rehabilitation session. All of this may be driven by the patient healthcare plan (PHP) as described in the HEALTHCARE DELIVERY SYSTEM AND METHOD patent application which may be run autonomously on the MUD without immediate interaction with a host computer system (HCS), permitting intermittent communication with the HSC to be sufficient to fully monitor and rehabilitate the patient without the need for immediate intervention by a healthcare professional. As stated previously, the rehabilitation AVI and PII obtained from the patient may be stored and later scored by a healthcare professional in situations where a live healthcare professional is not available or in situations where data communication between the MUD and HCS is compromised.

Exemplary Display Presentations (0400)

Figure 4:
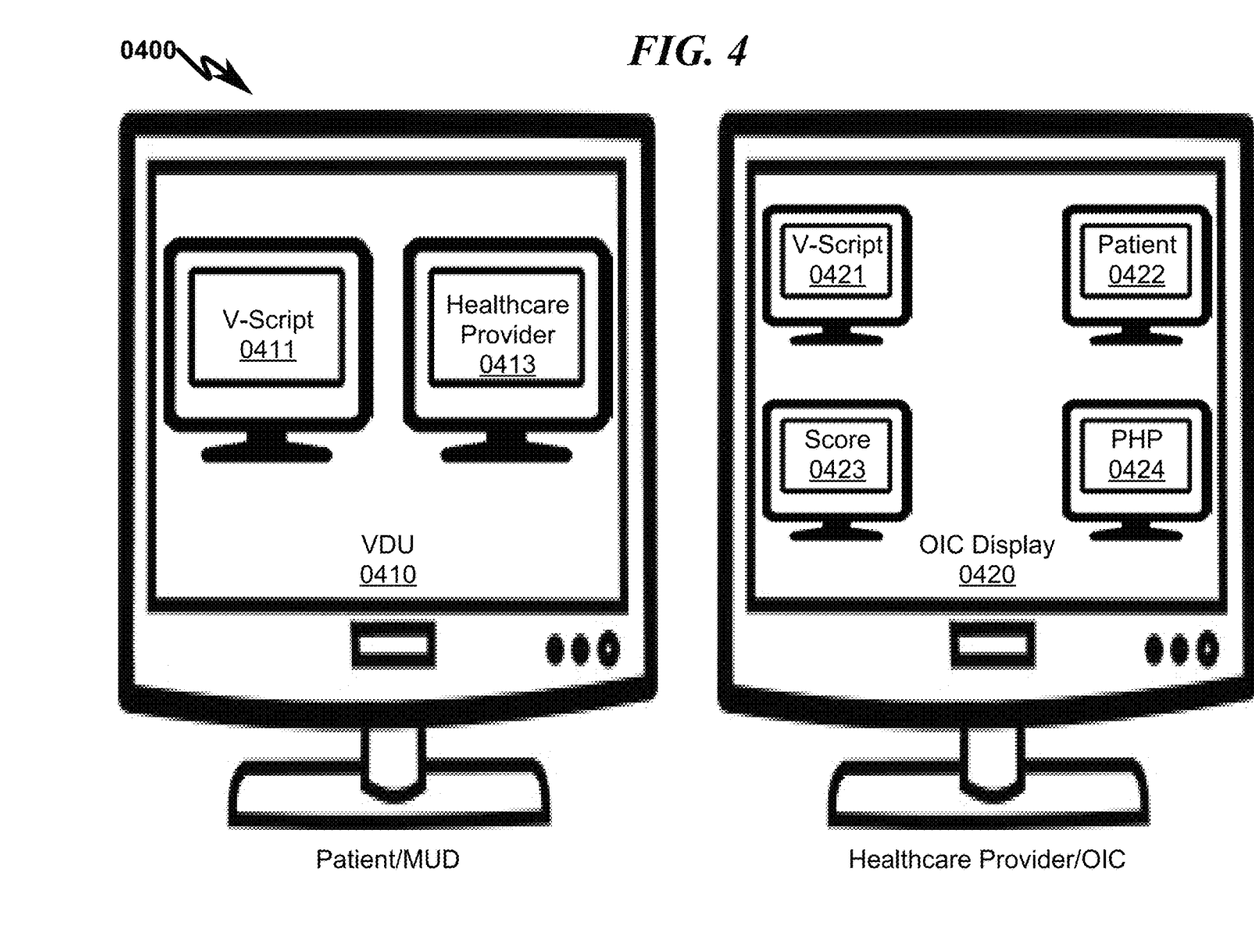
FIG. 4 illustrates exemplary patient and healthcare provider displays.

While the present invention anticipates that a variety of display presentations may be possible in a variety of invention embodiments, an exemplary display deployment is depicted in FIG. 4 (0400) wherein an exemplary patient display (0410) is presented and an exemplary healthcare provider display (0420) is presented for illustrative purposes.

The patient display (0410) may be typically deployed on a VDU (HDTV and/or MUD display, etc.) and include AVI content displayed under control of a video script (0411) that represents directions to the patient for exercises, movement, activity, etc. Simultaneously with this there may be a healthcare provider display (0412) that provides a real-time view of a healthcare provider that allows interaction between the patient and healthcare provider as the patient executes the directives provided on the rehabilitation video script display (0411).

The healthcare provider display (0420) may also incorporate a video script display (0421) in conjunction with a real-time patient display (0422) but will also incorporate a scoring display (0423) that permits the healthcare provider to score the activity of the patient at predefined times during the presentation of the video rehabilitation script to the patient display (0411) and healthcare provider display (0421). The real-time view of the patient (0422) may permit the healthcare provider to direct the patient to correct errors in rehabilitation activity or note problems with patient progress during the procedure. The scoring display (0423) may be configured to permit the healthcare provider the opportunity to log comments as to patient progress or other issues that should be of note in the patient medical history file. The healthcare provider display (0420) may also incorporate a view into the patient healthcare plan (PHP) for the patient to permit the healthcare provider the opportunity to modify the PHP based on the observed patient rehabilitation process. Since the PHP is the overall driving agent in the delivery of healthcare to the patient in this system, modification of the PHP can result in modification of the AVI content deployed to the patient via the video scripting system that drives the virtual rehabilitation system.

PHP Directed Patient Rehabilitation (0500)

Figure 5:
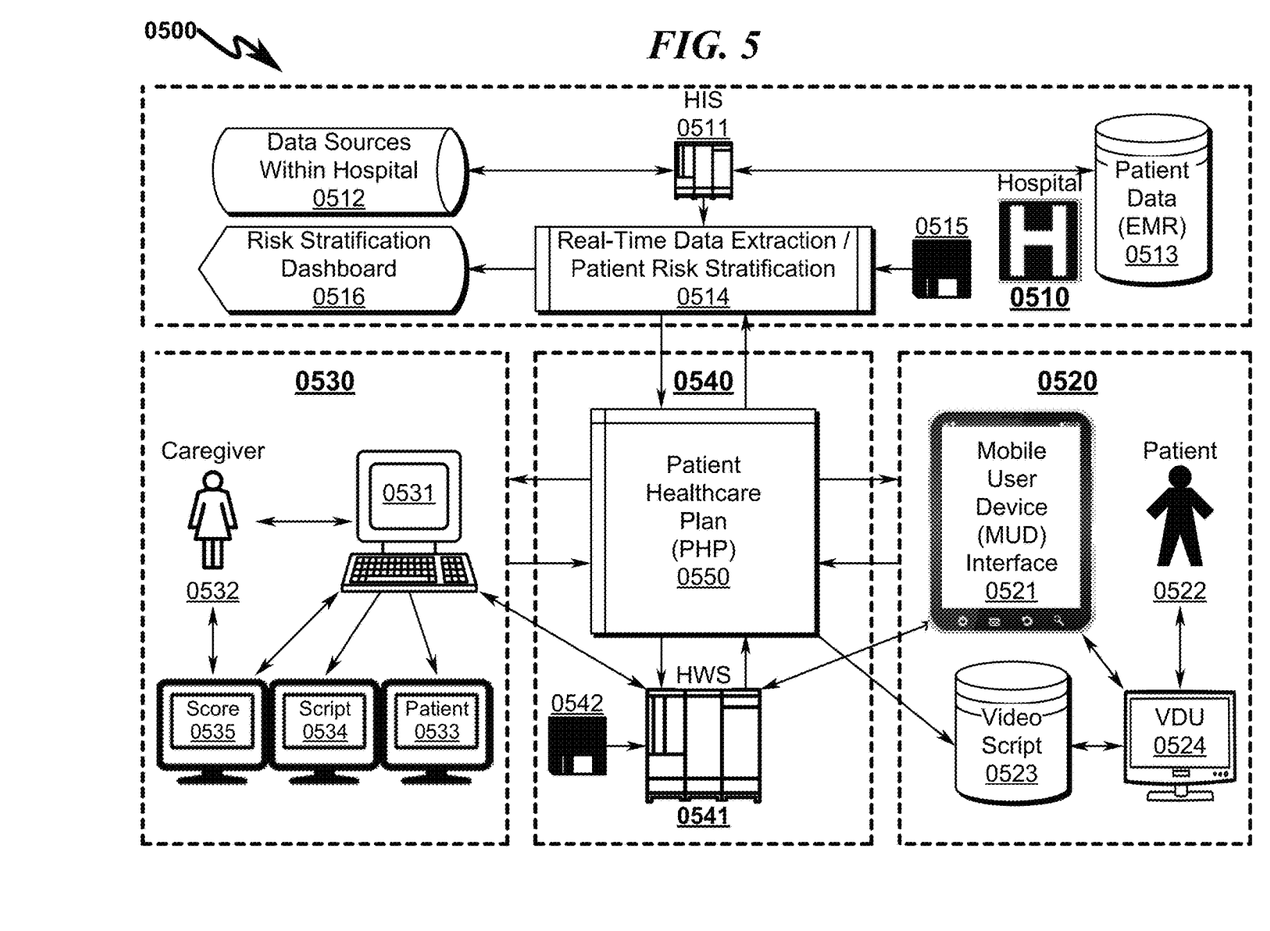
FIG. 5 illustrates a system block diagram depicting the interaction between a patient healthcare plan (PHP) and virtual rehabilitation system as described herein.

The HEALTHCARE DELIVERY SYSTEM AND METHOD patent application describes how a patient healthcare plan (PHP) may be defined by the host computer system (HCS) under direction of a healthcare management team to customize the healthcare given to a given patient. FIG. 5 (0500) depicts how this PHP-driven healthcare model may be adapted to integrate a virtual patient rehabilitation system. Here it can be observed that as described in the HEALTHCARE DELIVERY SYSTEM AND METHOD patent application the hospital environment (0510) incorporates a healthcare information system (HIS) (0511) that works in conjunction with patient environment (0520) incorporating a mobile user device (MUD) (0521) and a caregiver environment (0530) incorporating a computer interface (0531). All of these systems (0511, 0521, 0531) operate under direction of a PHP environment (0540) comprising a healthcare web server (HWS) (0541) that defines and drives a patient healthcare plan (0550) to the MUD (0521) for execution in the patient environment (0520) and simultaneously links real-time patient updates to the HIS (0511) system and caregiver interfaces (0531).

Integration of a virtual rehabilitation system/method in this context proceeds as follows. The PHP (0550) is configured to enable activation of video scripts (0523) within the patient environment (0520) to present information on a video display unit (VDU) (0524) and/or MUD (0521) to elicit rehabilitation activity or monitoring of the patient (0522) in response to predefined actions defined by a video. The video scripts (0523) are one of a number of actions that the PHP (0540) may direct the MUD (0521) to perform autonomously of the HWS (0541). The VIDEO DATA EXTENSION SYSTEM AND METHOD patent application describes how this video content may be spread across the MUD (0521) and/or VDU (0524) based on a user interaction context (UIC) defined by the PHP. The DYNAMIC VIDEO SCRIPTING SYSTEM AND METHOD patent application describes how the video scripts may be generated using a graphical user interface (GUI) so that generation of the video scripts can be accomplished by healthcare providers who may not necessarily have a high degree of computer literacy or computer programming skills.

The behavior of the patient (0522) in response to the video script (0523) is relayed to caregiver (0532) monitors (0533) in conjunction with the video script (0534) and scored (0525) by the caregiver at set points during the patient rehabilitation video script. Results of this scoring are then available for dissemination to authorized healthcare providers via the HWS (0541) and are updated to the patient medical records (0513). The result of this integration of the various computer systems (0511, 0521, 0531, 0541) is that all authorized healthcare providers have available a real-time status of patient progress and treatment.

Exemplary Virtual Rehabilitation Operation (0600)-(0800)

Figure 6:
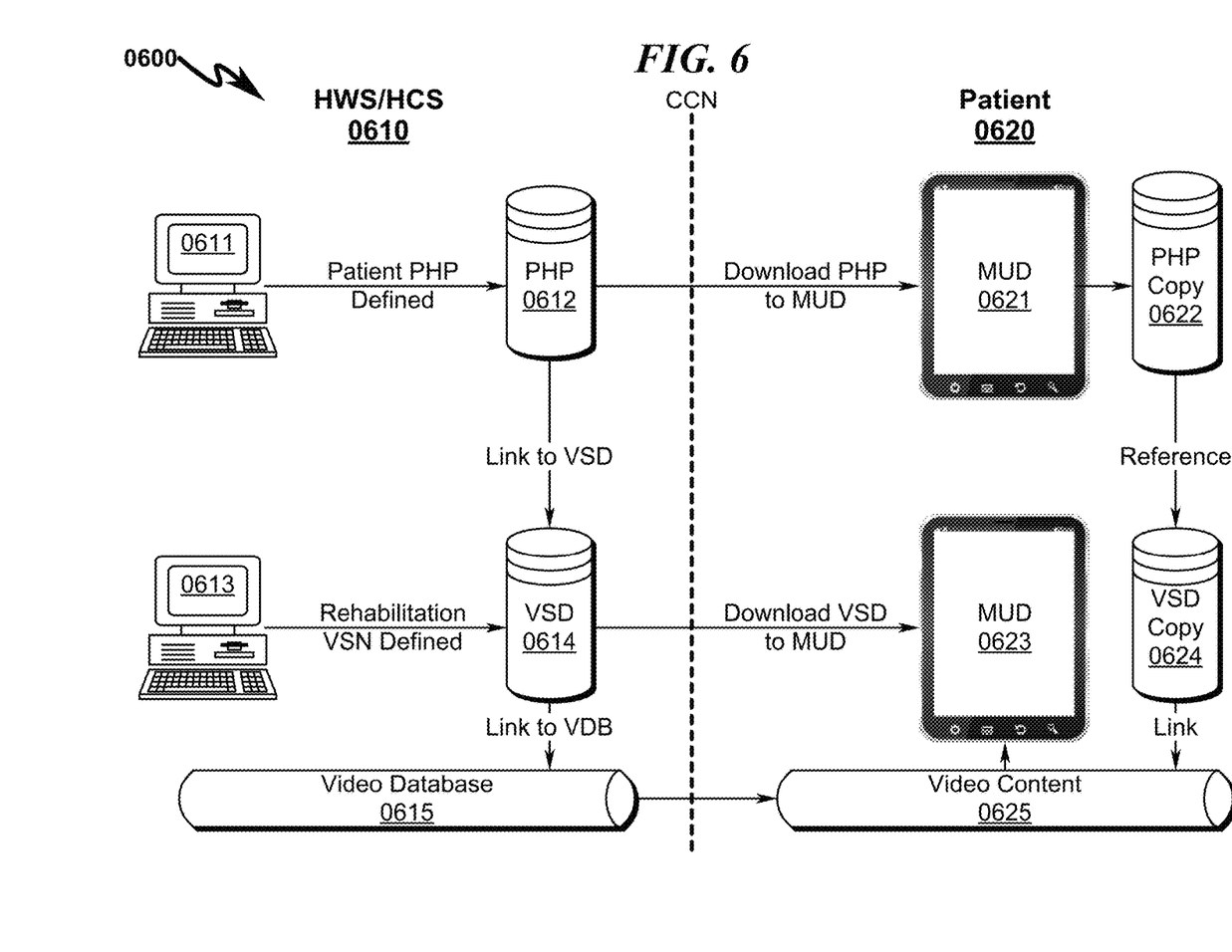
FIG. 6 illustrates exemplary sequencing for a virtual rehabilitation script operating in the context of a patient healthcare plan (PHP) (page 1/3)
Figure 7:
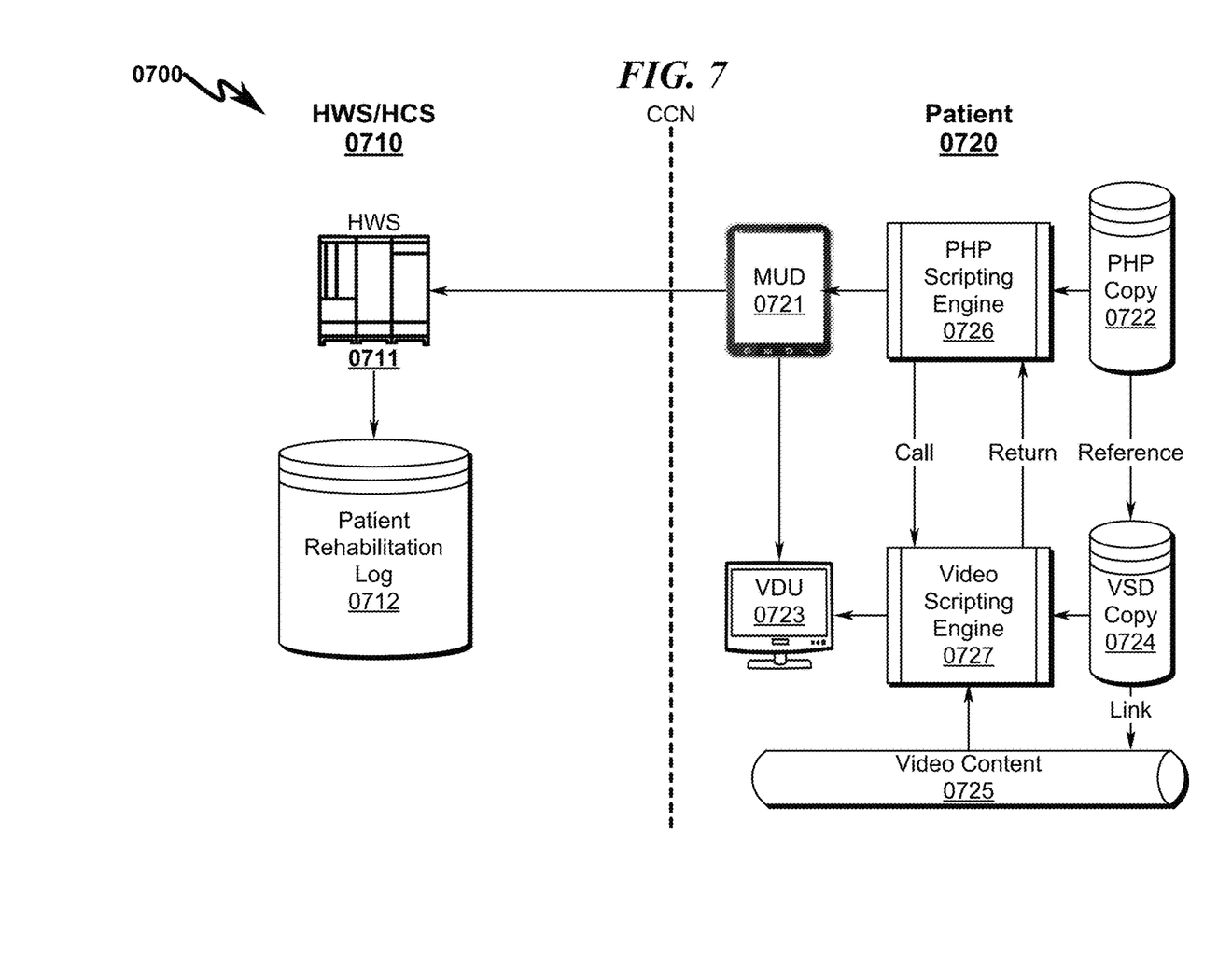
FIG. 7 illustrates exemplary sequencing for a virtual rehabilitation script operating in the context of a patient healthcare plan (PHP) (page 2/3)
Figure 8:
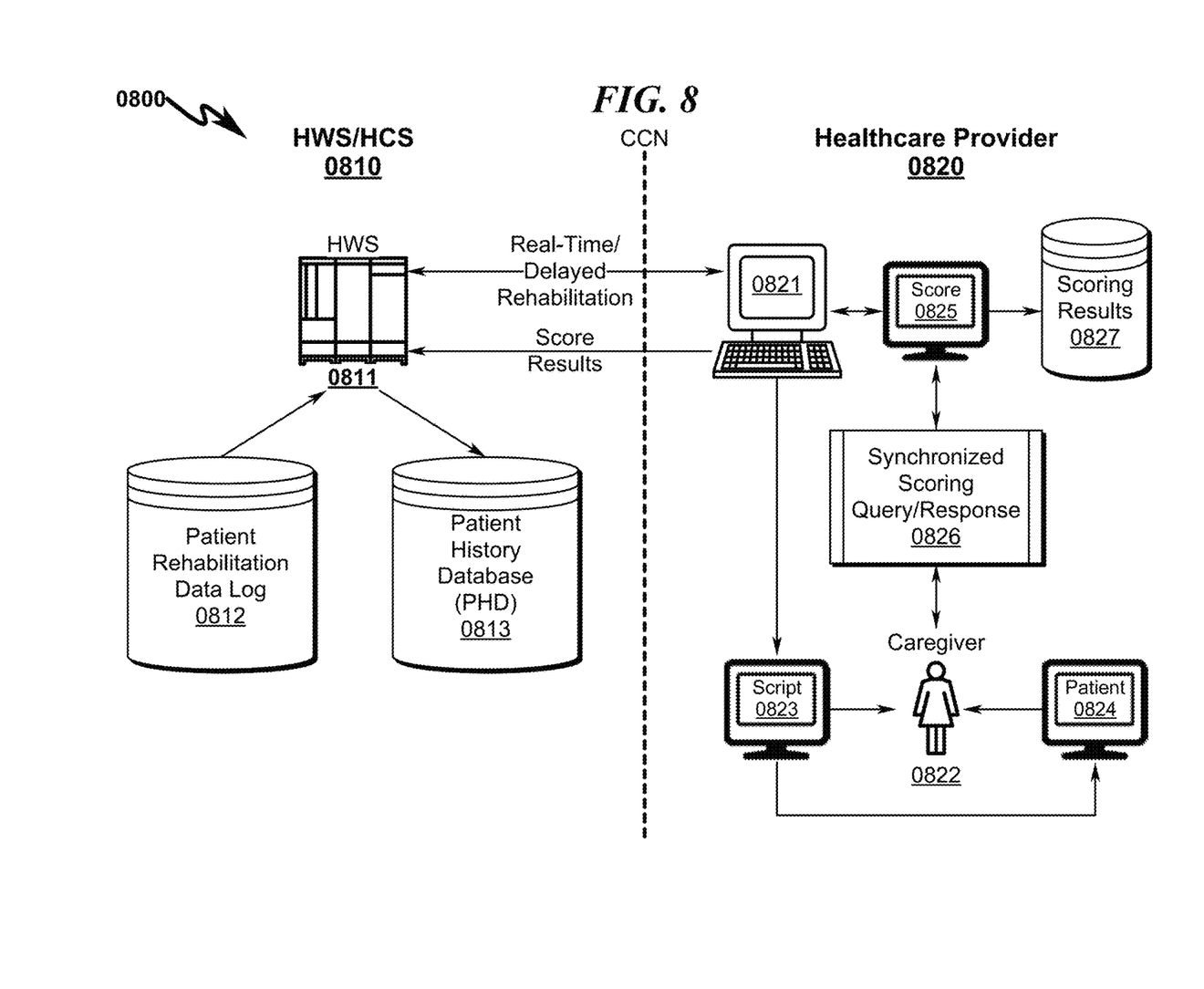
FIG. 8 illustrates exemplary sequencing for a virtual rehabilitation script operating in the context of a patient healthcare plan (PHP) (page 3/3).

An exemplary operational context for the virtual rehabilitation system and method is generally depicted in FIG. 6 (0600)-FIG. (0800). Here the healthcare web server (HWS) (also termed a host computer system (HCS)) context (0610, 0710, 0810) and remote patient context (0620, 0720, 0820) are depicted with information flows between the two contexts crossing the vertical dashed line via the computer communication network (CCN).

PHP/VSD Configuration (0600)

FIG. 6 (0600) generally depicts a healthcare provider interface (0611) used to create the PHP (0612) as generally described in the HEALTHCARE DELIVERY SYSTEM AND METHOD patent application. This PHP is then deployed to the MUD (0621) and stored locally (0622) to permit autonomous operation of the PHP (0612) within the MUD (0621) environment. The PHP (0612) as defined may also permit a healthcare provider interface (0623) to define a rehabilitation video scripting network (VSN) that is converted to a video scripting dataset (VSD) (0614). This VSN (0614) may incorporate references to a video database (VDB) (0615) and internal control structures to define interactions with the patient and/or medical instruments communicating with the MUD. This VSD (0614) is transferred to the MUD (0623) and stored locally (0624) along with any relevant video content (0625) that may be necessary to allow the video script to run autonomously on the MUD (0623).

PHP/VSD Execution (0700)

FIG. 7 (0700) depicts typical autonomous operation of the virtual rehabilitation system/method. Here the MUD (0721) executes the PHP (0722) in the context of a PHP scripting engine (0726) that may perform a wide variety of patient interactions with the patient using both synchronous and asynchronous operations as described in the HEALTHCARE DELIVERY SYSTEM AND METHOD patent application. One of these operations may involve triggering a virtual rehabilitation session and executing a VSD (0724) video script via calling the video scripting engine (0727) to queue the appropriate video to the patient, record the patient responses, and permit live interaction with a healthcare provider if necessary. This video script is generally presented on a video display unit (0723) and may contain a variety of downloaded video content (0725) that has been preloaded so as to permit autonomous operation of the rehabilitation session if necessary.

The data associated with the patient responses to the VSD (0724) and rehabilitation video content (0725) is relayed by the MUD (0721) to the HWS (0711) for storage in a patient rehabilitation log (0712) that is associated with the patient history database (PHD). This information may not necessarily be stored in real-time, but rather queued for storage by the MUD (0721) depending on the status of the CCN linking the HWS (0711) and MUD (0721) as described in the HEALTHCARE DELIVERY SYSTEM AND METHOD patent application.

Rehabilitation Scoring (0800)

The presentation of a rehabilitation video script to the patient as depicted in FIG. 7 (0700) requires evaluation of the patient response to the rehabilitation directives defined by the VSD. This may be accomplished either in real-time or on a delayed basis as depicted in FIG. 8 (0800). Here the HWS (0811) relays the patient rehabilitation data log (0812) (comprising information associated with the VSD rehabilitation activity with the patient depicted in FIG. 7 (0700)) to an operator interface computer (OIC) (0821) that interfaces with a healthcare caregiver/provider (0822). The OIC (0821) presents both the video script (0822) presented to the patient as well as a view of the patient responses (0824) to allow the caregiver (0822) to compare the directed patient response and the actual patient response. At set points during this display/review process a scoring display (0825) will be presented to the caregiver (0822) under control of a synchronized scoring query/response process that allows patient performance metrics to be queried to the caregiver (0822) and the patient rehabilitation performance to be logged on the scoring display (0825) and stored (0827) for transmission to the HWS (0811) and incorporation into the patient history database (PHD) (0813).

As indicated in this diagram, the evaluation of the patient rehabilitation performance may occur in real-time or be delayed after the fact by simply reviewing the script (0823) and patient (0824) performance in a synchronized fashion under control of the scoring process (0826). Since the MUD in this configuration is capable of store-and-forward with respect to patient alerts and other data to the HWS, this permits patient rehabilitation to occur in situations where the data link between the MUD and HWS is compromised or unavailable.

Note that the synchronized scoring query/response process (0826) may be incorporated as a sub-function within the VSD data structure and be interpreted to generate scoring synchronization markers within the VSD for action by software not necessarily associated with the presentation of the video script to the patient. In other words, the present invention anticipates that synchronization markers as described in the DYNAMIC VIDEO SCRIPTING SYSTEM AND METHOD patent application may be used by the query/response (0826) process to elicit information from the caregiver (0822) as to the scoring of patient rehabilitation. In this context the synchronization information contained in the VSD is not presented to the patient but represents a separate internal data thread within the VSD that allows post-processing activity by other software that is not necessarily associated with the patient display process.

Preferred Embodiment System Summary

The present invention preferred exemplary system embodiment anticipates a wide variety of variations in the basic theme of construction, but can be generalized as a virtual rehabilitation system comprising:
(a) host computer system (HSC);
(b) mobile user device (MUD);
(c) video display unit (VDU);
(d) video imaging unit (VIU);
(e) operator interface computer (OIC); and
(f) computer communication network (CCN);
wherein the HCS is configured to retrieve audio/video information (AVI) from a video database (VDB) under control of a video script dataset (VSD);

the MUD is configured to coordinate transmission of the AVI to the VDU via the CCN;

the MUD is configured to coordinate display of the AVI on the VDU for presentation to a patient;

the MUD is configured to collect patient imaging input (PII) associated with reaction of the patient to the AVI from the VIU;

the MUD is configured to coordinate transmission of the AVI and the PII to the OIC via the CCN;

the OIC is configured to present a visual display of the AVI and the PII;

the OIC is configured to accept synchronized scoring inputs (SSI) responsive to the visual display;

the OIC is configured to transmit the SSI to the HCS via the CCN; and the HCS is configured to store the SSI in a patient history database (PHD).

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a virtual rehabilitation method comprising:

(1) with a host computer system (HSC), retrieving audio/video information (AVI) from a video database (VDB) under control of a video script dataset (VSD);

(2) with a mobile user device (MUD), coordinating transmission of the AVI to a video display unit (VDU) via a computer communication network (CCN);

(3) with the MUD, coordinating display of the AVI on the VDU for presentation to a patient;

(4) with the MUD, collecting patient imaging input (PII) associated with reaction of the patient to the AVI from a video imaging unit (VIU);

(5) with the MUD, coordinating transmission of the AVI and the PII to an operator interface computer (OIC) via the CCN;

(6) with the OIC, presenting a visual display of the AVI and the PII;

(7) with the OIC, accepting synchronized scoring inputs (SSI) responsive to the visual display;

(8) with the OIC, transmitting the SSI to the HCS via the CCN; and (9) with the HCS, storing the SSI in a patient history database (PHD).

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the CCN comprises the Internet.

An embodiment wherein the VSD is triggered by a patient healthcare plan (PHP) sourced by the HCS and transmitted to the MUD via the CCN.

An embodiment wherein the visual display further comprises a display of a performance metric standard associated with the AVI display.

An embodiment wherein the visual display further comprises a visual display of prior performance of the patient retrieved by the OIC from the PHD via the HCS.

An embodiment wherein the SSI triggered by primitives within the VSD.

An embodiment wherein the MUD further comprises the VIU.

An embodiment wherein the VDU is configured to present a user interaction context (UIC) comprising the AVI and real-time video captured by the OIC.

An embodiment wherein the OIC is configured to record the AVI and the PII and display this recorded AVI/PII information at a later time and at the later time accept delayed entry of the SSI.

An embodiment wherein the AVI further comprises a real-time video retrieved from the OIC.

An embodiment wherein the visual display further comprises a patient healthcare plan (PHP).

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method providing virtual physical rehabilitation services to a patient in the context of automated patient healthcare delivery has been disclosed. The system/method are controlled by a patient healthcare plan (PHP) deployed from a host computer system (HCS) that triggers execution of a video script dataset (VSD) to coordinate presentation to a patient of rehabilitation audio/video information (AVI) derived from a video database (VDB). A mobile user device (MUD) executes the PHP autonomously to coordinate AVI display on a video display unit (VDU) for patient presentation. Patient reactions to the AVI are observed by a video imaging unit (VIU). An operator interface computer (OIC) communicates with the HCS and MUD permitting visualization of the VIU and AVI information by a healthcare provider and allowing observed patient behavior to be synchronously scored/logged/stored in a patient history database (PHD) by the HCS.

Although a preferred embodiment of the present invention has been illustrated in the accompanying drawings and described in the foregoing Detailed Description, it will be understood that the invention is not limited to the embodiments disclosed, but is capable of numerous rearrangements, modifications, and substitutions without departing from the spirit of the invention as set forth and defined by the following claims.

Within the context of the following CLAIMS, the CLAIM PREAMBLE should be considered as limiting the scope of the claimed invention. Within the context of the following CLAIMS, "wherein" clauses should be considered as limiting the scope of the claimed invention. The phrase "and/or" in the context of an expression "X and/or Y" should be interpreted to mean the set of "(X and Y)" in union with the set "(X or Y)."

What is claimed is:

1. A virtual rehabilitation system comprising:
   (a) host computer system (HCS);
   (b) mobile user device (MUD);
   (c) video display unit (VDU);
   (d) video imaging unit (VIU);
   (e) operator interface computer (OIC); and
   (f) computer communication network (CCN);
   wherein
   said HCS is configured to retrieve audio/video information (AVI) from a video database (VDB) under control of a patient healthcare plan (PHP) tailored for a patient, wherein said PHP comprises a video script dataset (VSD), wherein said VSD describes an interaction with said patient via the controlled display of said AVI extracted from said VDB;
   said MUD is configured to execute said PHP autonomously upon receipt of said PHP from said HCS;
   said MUD, under control of said PHP, is configured to coordinate transmission of said AVI to said VDU based on said PHP via said CCN;
   said MUD is configured to coordinate simultaneous display of said AVI and of a real-time display of a healthcare provider on said VDU for presentation to said patient;
   said MUD is configured to collect patient imaging input (PII) associated with reaction of said patient to said AVI from said VIU;
   said MUD is configured to coordinate transmission of said AVI and said PII to said OIC via said CCN;
   said OIC is configured to present a simultaneous visual display of said PHP, said AVI and said PII;
   said OIC is configured to accept synchronized scoring inputs (SSI) responsive to said visual display and to accept PHP modifications;
   said OIC is configured to transmit said SSI and PHP modifications to said HCS via said CCN;
   said HCS is configured to update said AVI responsive to said PHP modifications, and to update said PHP based on said PHP modifications to generate an updated PHP;
   said HCS is configured to automatically transfer said updated PHP to said MUD via said CCN;
   said MUD is configured to execute said updated PHP autonomously upon receipt of said updated PHP from said HCS; and
   said HCS is configured to store said SSI in a patient history database (PHD).

2. The virtual rehabilitation system of claim 1 wherein said visual display further comprises a display of a performance metric standard associated with said AVI display.

3. The virtual rehabilitation system of claim 1 wherein said visual display further comprises a visual display of prior performance of said patient retrieved by said OIC from said PHD via said HCS.

4. The virtual rehabilitation system of claim 1 wherein said SSI triggered by primitives within said VSD.

5. The virtual rehabilitation system of claim 1 wherein said MUD further comprises said VIU.

6. The virtual rehabilitation system of claim 1 wherein said VDU is configured to present a user interaction context (UIC) comprising said AVI and real-time video captured by said OIC.

7. The virtual rehabilitation system of claim 1 wherein said OIC is configured to record said AVI and said PII and display this recorded AVI/PII information at a later time and at said later time accept delayed entry of said SSI.

8. The virtual rehabilitation system of claim 1 wherein said AVI further comprises a real-time video retrieved from said OIC.

9. A virtual rehabilitation method comprising:
   (1) with a host computer system (HCS), retrieving audio/video information (AVI) from a video database (VDB) under control of a patient healthcare plan (PHP) tailored for a patient, wherein said PHP comprises a video script dataset (VSD), wherein said VSD describes an interaction with said patient via a controlled display of said AVI extracted from said VDB;
   (2) with a mobile user device (MUD), executing said PHP autonomously upon receipt of said PHP from said HCS;
   (3) with said MUD under control of said PHP, coordinating transmission of said AVI to a video display unit (VDU) based on said PHP via a computer communication network (CCN);
   (4) with said MUD, coordinating simultaneous display of said AVI and of a real-time display of a healthcare provider on said VDU for presentation to said patient;
   (5) with said MUD, collecting patient imaging input (PII) associated with reaction of said patient to said AVI from a video imaging unit (VIU);
   (6) with said MUD, coordinating transmission of said AVI and said PII to an operator interface computer (OIC) via said CCN;
   (7) with said OIC, presenting a simultaneous visual display of said PHP, said AVI and said PII;

(8) with said OIC, accepting synchronized scoring inputs (SSI) responsive to said visual display and accepting PHP modifications;
(9) with said OIC, transmitting said SSI to said HCS via said CCN;
(10) with said HCS, updating said AVI responsive to said PHP modifications and updating said PHP based on said PHP modifications to generate an updated PHP;
(11) with said HCS, automatically transfer said updated PHP to said MUD via said CCN; and
(12) with said HCS, storing said SSI in a patient history database (PHD).

10. The virtual rehabilitation method of claim 9 wherein said visual display further comprises a display of a performance metric standard associated with said AVI display.

11. The virtual rehabilitation method of claim 9 wherein said visual display further comprises a visual display of prior performance of said patient retrieved by said OIC from said PHD via said HCS.

12. The virtual rehabilitation method of claim 9 wherein said SSI triggered by primitives within said VSD.

13. The virtual rehabilitation method of claim 9 wherein said MUD further comprises said VIU.

14. The virtual rehabilitation method of claim 9 wherein said VDU is configured to present a user interaction context (UIC) comprising said AVI and real-time video captured by said OIC.

15. The virtual rehabilitation method of claim 9 wherein said OIC is configured to record said AVI and said PII and display this recorded AVI/PII information at a later time and at said later time accept delayed entry of said SSI.

16. The virtual rehabilitation method of claim 9 wherein said AVI further comprises a real-time video retrieved from said OIC.

17. A tangible non-transitory computer usable medium having computer-readable program code means embodied thereon comprising a virtual rehabilitation method comprising:
(1) with a host computer system (HCS), retrieving audio/video information (AVI) from a video database (VDB) under control of a patient healthcare plan (PHP) tailored for a patient, wherein said PHP comprises a video script dataset (VSD), wherein said VSD describes an interaction with said patient via a controlled display of said AVI extracted from said VDB;
(2) with a mobile user device (MUD), executing said PHP autonomously upon receipt of said PHP from said HCS;
(3) with said MUD under control of said PHP, coordinating transmission of said AVI to a video display unit (VDU) based on said PHP via a computer communication network (CCN);
(4) with said MUD, coordinating simultaneous display of said AVI and of a real-time display of a healthcare provider on said VDU for presentation to said patient;
(5) with said MUD, collecting patient imaging input (PII) associated with reaction of said patient to said AVI from a video imaging unit (VIU);
(6) with said MUD, coordinating transmission of said AVI and said PII to an operator interface computer (OIC) via said CCN;
(7) with said OIC, presenting a simultaneous visual display of said PHP, said AVI and said PII;
(8) with said OIC, accepting synchronized scoring inputs (SSI) responsive to said visual display and accepting PHP modifications;
(9) with said OIC, transmitting said SSI to said HCS via said CCN;
(10) with said HCS, updating said AVI responsive to said PUP modifications and updating said PHP based on said PHP modifications to generate an updated PHP;
(11) with said HCS, automatically transfer said updated PHP to said MUD via said CCN; and
(12) with said HCS, storing said SSI in a patient history database (PHD).

18. The computer usable medium of claim 17 wherein said visual display further comprises a display of a performance metric standard associated with said AVI display.

19. The computer usable medium of claim 17 wherein said visual display further comprises a visual display of prior performance of said patient retrieved by said OIC from said PHD via said HCS.

20. The computer usable medium of claim 17 wherein said SSI triggered by primitives within said VSD.

21. The computer usable medium of claim 17 wherein said MUD further comprises said VIU.

22. The computer usable medium of claim 17 wherein said VDU is configured to present a user interaction context (UIC) comprising said AVI and real-time video captured by said OIC.

23. The computer usable medium of claim 17 wherein said OIC is configured to record said AVI and said PII and display this recorded AVI/PII information at a later time and at said later time accept delayed entry of said SSI.

24. The computer usable medium of claim 17 wherein said AVI further comprises a real-time video retrieved from said OIC.

* * * * *